(12) United States Patent
Cao et al.

(10) Patent No.: US 7,069,085 B2
(45) Date of Patent: Jun. 27, 2006

(54) METHOD AND APPARATUS TO PRODUCE, MAINTAIN AND REPORT INFORMATION RELATED TO PATIENT TREATMENT USING MEDICAL DEVICES

(75) Inventors: Wei Cao, Shoreview, MN (US); Par Lindh, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 644 days.

(21) Appl. No.: 10/235,176

(22) Filed: Sep. 5, 2002

(65) Prior Publication Data

US 2004/0049244 A1    Mar. 11, 2004

(51) Int. Cl.
*A61N 1/08* (2006.01)

(52) U.S. Cl. .......................................... 607/60; 607/32

(58) Field of Classification Search ............. 607/30–32, 607/59–60; 128/903
See application file for complete search history.

(56) References Cited

U.S. PATENT DOCUMENTS 5,724,985 A * 3/1998 Snell et al. .................. 600/510
6,558,321 B1 * 5/2003 Burd et al. .................. 600/300

* cited by examiner

*Primary Examiner*—Robert E. Pezzuto
*Assistant Examiner*—Kristen Mullen
(74) *Attorney, Agent, or Firm*—Thomas J. Nikolai; Nikolai & Mersereau, P.A.

(57) ABSTRACT

A system for automating the process of generating reports, such as warranty and registration reports, for programmable medical devices. The system uses a variety of data collecting and checking techniques to make the generator and transmission of such reports more efficient.

42 Claims, 6 Drawing Sheets

FIG. 2
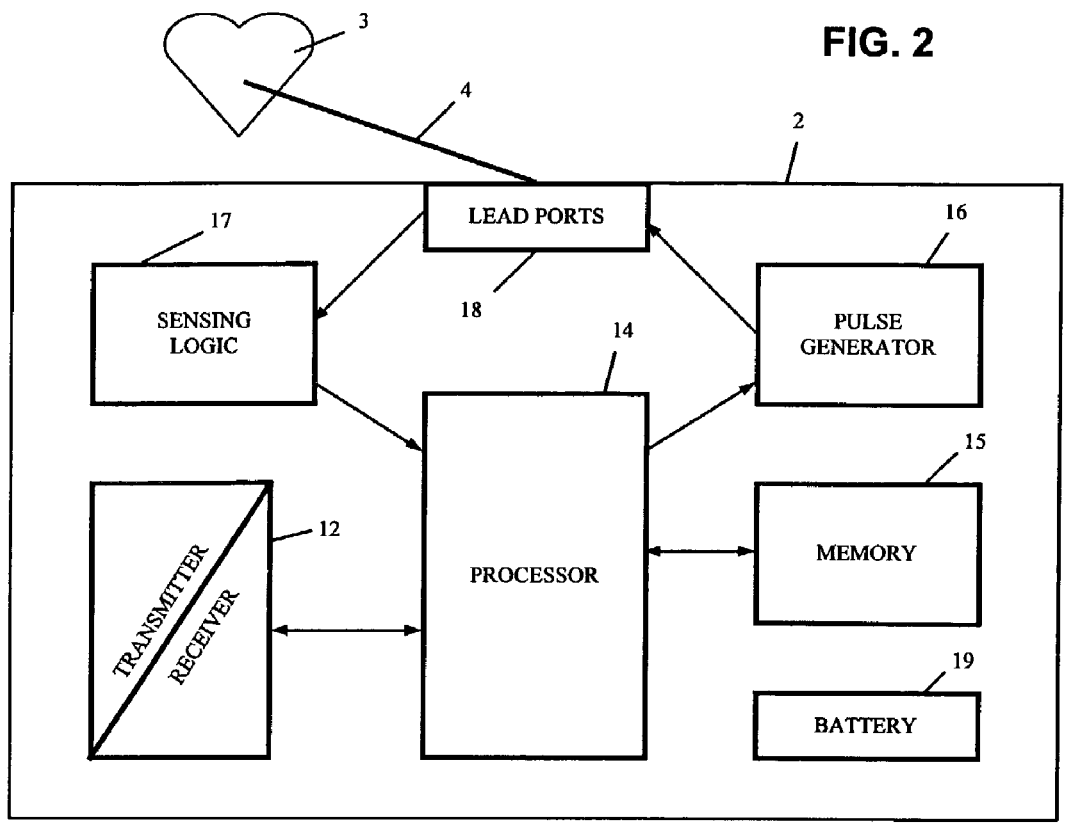
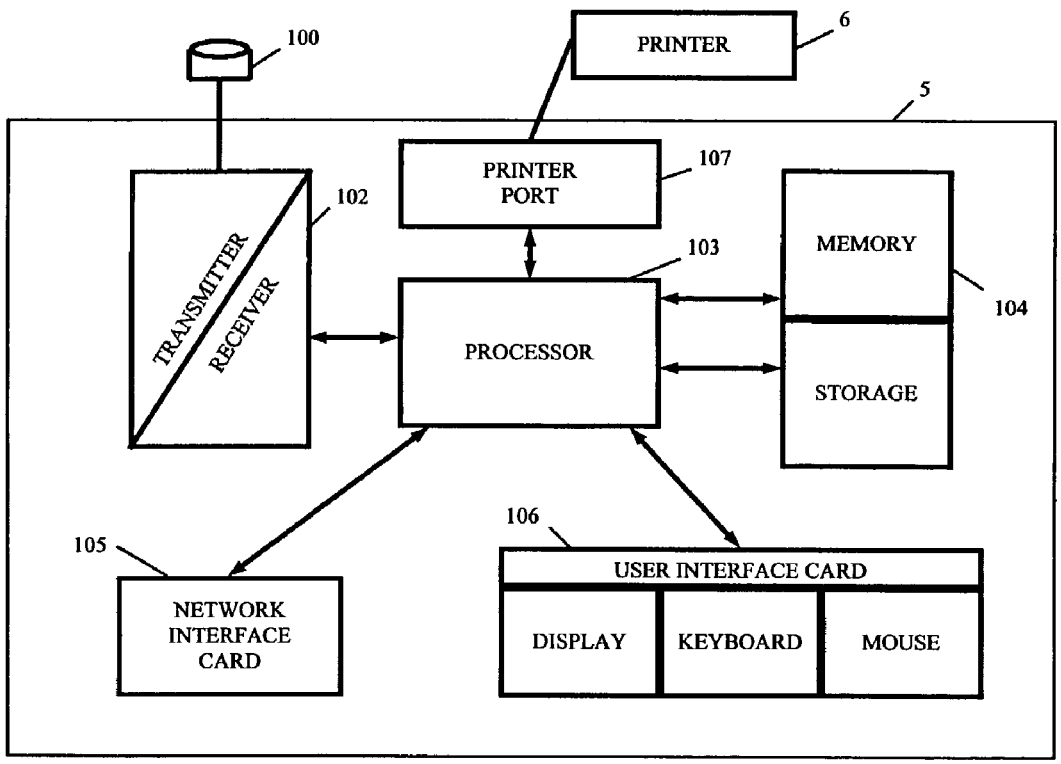

FIG. 5

Complete all information. Type or print legibly. Press hard.
Return original copy to Guidant in the envelope provided.

GUIDANT
355910-001 A

IMPORTANT: Federal regulations require the distribution and/or implant of this device to be tracked and reported to Guidant.

HEART FAILURE DEVICE WARRANTY VALIDATION AND LEAD REGISTRATION

Device Identification
Place label here on each copy or fill in
PG Model Number | Serial Number
Implant Date: MM-DD-YYYY

PATIENT INFORMATION (Please print or type)
Last Name | First Name | MI | Suffix | Phone
Address | City | State | Zip Code + Four
Social Security Number | Date of Birth MM-DD-YYYY | Gender: Male / Female | Country: USA / OTHER

PHYSICIAN INFORMATION
Implanting Physician (Last, First) | Surg / EP / Card / OTHER | MI | Suffix | Phone
Address | City | State | Zip Code + Four Following Physician (Last, First) (If other than Implanting) | EP / Card / OTHER | MI | Suffix | Phone
Address | City | State | Zip Code + Four

IMPLANTING HEALTH CARE FACILITY
Facility Name | Phone
Address | City | State | Zip Code + Four

IMPLANTED LEAD INFORMATION
Place label(s) here on each copy or fill in

| Implant Date | Model | Serial Number | Distal Polarity | Lead Position |
|---|---|---|---|---|
| MM DD YYYY | | | +/UNI, -/BI | RA / LV (CS) / RA/RV (ENDOTAK), RV / SQ-LLC / OTHER |
| MM DD YYYY | | | +/UNI, -/BI | RA / LV (CS) / RA/RV, RV / SQ-LLC / OTHER |
| MM DD YYYY | | | +/UNI, -/BI | RA / LV (CS) / RA/RV, RV / SQ-LLC / OTHER |
| MM DD YYYY | | | +/UNI, -/BI | RA / LV (CS) / RA/RV, RV / SQ-LLC / OTHER |

Concomitant Pacemaker?
No / Yes (Indicate the manufacturer) Guidant / OTHER
Mode | PG Model Number | Serial Number
Polarity: UNI / BI
Place label here on each copy or fill in

Were any PULSE GENERATORS explanted?
No / Yes (Indicate the manufacturer) Guidant / OTHER Check all that apply:
- Normal battery depletion
- Elective replacement
- Dissatisfied with product (describe below)
- Advisory/recall
- Product performance issue (describe below)

Model Number | Serial Number
Explant Date MM-DD-YYYY

Please describe (attach additional sheets if necessary)
DESCRIBE

Were any of this patient's leads removed from service for reasons stated above? No / Yes   If yes, list any lead removed from service or modified from its original condition.

Model Number | Serial Number | Out-of-Service Date MM-DD-YYYY | DESCRIBE CHANGE/REASON
Model Number | Serial Number | Out-of-Service Date MM-DD-YYYY | DESCRIBE CHANGE/REASON

Were complications experienced during implant? No / Yes   If yes, complete the Observation/Complication/Out-of-Service Reporting Form and send to Guidant.

NOTE: To enable processing of this warranty validation form, please provide (do not staple or tape) the following reports, Patient Data, Quick Notes, along with this completed form to Guidant.

COMMENTS

24-HOUR CONSULTATION
Worldwide: 651-582-4000
USA: 1-800-CARDIAC
(1-800-227-3422)

FILLED OUT BY (Please print)
Name | Phone
Position/Title | Date MM-DD-YYYY

Guidant Corporation
Cardiac Rhythm Management
4100 Hamline Avenue North
St. Paul, MN 55112-5798

© 2000 Guidant Corporation
Printed USA. 9/00

Thank you for providing us with this information. If you have any questions or comments, please contact Guidant at 1-800-PATDATA (1-800-728-3282).

Original—Guidant Medical Records        Second Copy—Physician/Patient File        Third Copy—Hospital File

FIG. 6

METHOD AND APPARATUS TO PRODUCE, MAINTAIN AND REPORT INFORMATION RELATED TO PATIENT TREATMENT USING MEDICAL DEVICES

BACKGROUND OF THE INVENTION

I. Field of the Invention

This invention relates to medical devices such as heart pacemakers, defibrillators, leads and the like. More specifically, the invention relates to the creation and maintenance of records related to such medical devices to ensure proper medical care, to assist in medical research, and to comply with existing governmental regulations.

II. Description of the Related Art

The use of medical devices to treat a variety of medical conditions has increased dramatically over the past 40 years. Such devices, and particularly cardiac rhythm management devices, have become more sophisticated. Many features of these and other electronic implantable medical devices are now programmable so that the functionality of such devices can be uniquely tailored to address the specific needs of the patient who is the recipient of the implant. To ensure proper ongoing care of the patient, it is important to accurately document for future reference certain information related to the patient, the implantable device, and the manner in which the device is being used.

The state of medical care would not be as advanced as it is today were it not for the meticulous collection and analysis of patient data to determine the efficacy of various treatment methods. Such data not only assists medical researchers and medical providers to determine which courses of treatment work best, but also provide important information to determine what new courses of treatment might prove to be effective. Thus, researchers and companies involved in the development of medical products have a real need for high quality data.

With the advent of new medical technologies, various government agencies have required better recordkeeping and reporting. The current state of the art typically requires the medical provider to select one or more forms, manually complete the forms, make the requisite number of copies of the form, find the patient file and place a copy in the file, give copies to the patient, and mail copies to the device manufacturer. The creation of such records and reporting of data can thus be a time-consuming venture that greatly increases the cost of providing medical services and products to the public. Thus, a real need has developed for a way to provide greater efficiency in the recording and reporting of data.

State of the art implantable cardiac rhythm management devices and programmers for such devices are all capable of storing various types of data in their memories. The programmers have been used to retrieve data from the implantable device. The programmers have also been used to display and print various reports based on such data. However, the capabilities of such implantable devices and programmers have never been used to select the proper warranty and registration form for the particular implanted device, complete the form, print copies of the form or otherwise transmit the data contained on the form to facsimile machines at remote locations or to other remote devices such as a hospital's computer, a clinic's computer or a manufacturer's computer.

SUMMARY OF THE INVENTION

One object of the present invention is to provide greater efficiency in the creation and maintenance of records related to implantable medical devices.

Another object of the present invention is to create and maintain warranty and registration records related to implantable medical devices with a high degree of accuracy and efficiency.

Still another object of the present invention is to create such warranty and registration records using the programmer for implantable medical devices.

A further object of the present invention is to use the programmer to identify the implanted device, select the proper form for the device, and provide the information required by the form.

Still a further object of the present invention is the ability to use the programmer to print the completed forms and/or transmit the information to one or more remote devices such as a hospital's clinics or manufacturer's computer.

These and other objects and advantages of the present invention will become clear from a reading of the detailed description of the preferred embodiment in view of the accompanying drawings.

BRIEF DESCRIPTION OF THE DRAWINGS

FIG. 2 is a block diagram of a cardiac rhythm management device and programmer;

FIG. 5 is a sample warranty and registration form for a cardiac pacemaker; and

FIG. 6 is a sample of a form used for a heart failure device.

DETAILED DESCRIPTION OF THE PREFERRED EMBODIMENT

The present invention will be described in conjunction with its application to record keeping for cardiac rhythm management devices. However, this invention can be applied to other types of medical devices. Its application is also not restricted to implantable devices.

Figure 1:
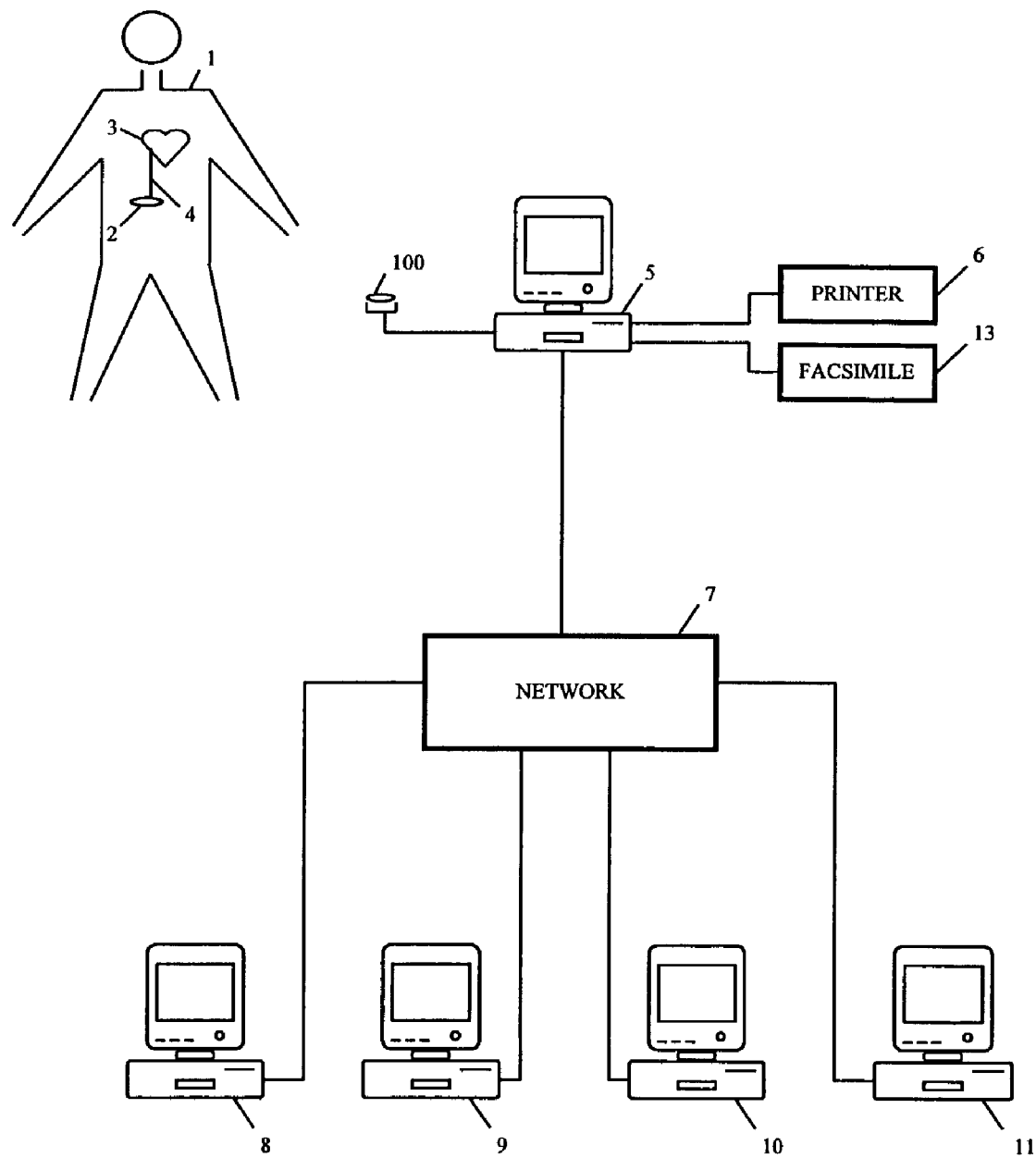
FIG. 1 is a block diagram showing various components of the system of the present invention.

FIG. 1 shows a patient 1. A cardiac rhythm management device 2 (sometimes referred to as a pulse generator) has been implanted and connected to the patient's heart 3 by a lead 4. Those skilled in the art will recognize that while a single lead is shown, often times multiple lead systems are used to sense cardiac activity and deliver electrical stimulation pulses to the heart 3. FIG. 1 also shows a programmer 5 having a communications wand 100 for communicating with the implanted cardiac rhythm management device 2. Also attached to the programmer 5 is a printer 6. The programmer 5 can also communicate with facsimile machine 13 via a telephone line or the like.

The programmer 5 can be linked to a network 7 of computers in any of a variety of ways. For purposes of example, other computers on the network 7 are the hospital's computer 8, the electrophysiologist's computer 9, the computer operated by patient's primary care physician 10, and the device manufacturer's computer 11. Virtually any number of computers can be on the network. In fact, if the programmer 5 is provided access to the Internet, the Internet can serve as the network 7 for data transmission between the programmer 5 and any of a variety of computers. As shown, the programmer 5 is one node on the network 7 and the computers 8–11 are also each separate nodes on the network 7.

Various types of cardiac rhythm management devices 2 exist today. Such types include pacemakers, defibrillators, cardiac resynchronization devices, and combination devices. Various models are made by a variety of manufacturers. Likewise, various types of leads and lead systems 4 exist. The warranty validation and lead registration information required depends upon the type of device 2 and lead system 4 implanted, the manufacturer, and the model.

In the past, warranty and registration cards were typically included within the packaging for the device 2 and lead system 4. The cards had to be manually completed. Data entry was, thus, susceptible to human error resulting from transposition of characters or the like. Errors can even occur because the wrong forms are used. The present invention reduces the errors associated with selecting the correct form and completing the necessary information.

FIG. 2 is a simple block diagram of a cardiac rhythm management device 2 and programmer 5. As shown, the cardiac rhythm management device 2 includes a transmitter/receiver 12 for two-way communication via wand 100 with the transmitter/receiver 102 of the programmer 5. The cardiac rhythm management device 2 also includes a processor 14 and a memory 15. The memory 15 stores information that can be used to identify a particular device 2 such as its manufacturer, serial number and model number. Memory 15 is also used to store a variety of information related to the operation of the device. For example, the memory 15 stores thresholds and parameters used by the processor 14 to control the delivery of electrical pulses by the pulse generator 16 via the lead system 4 to the heart 3 based upon signals received by the sensing logic 17 via the lead system 4 and lead ports 18. Such programmed parameters for a pacemaker can include the modes of operation, the lower rate and upper rate for delivery of pulses, the paced atrial-ventricular (AV) delay, the sensed AV delay and the dynamic AV delay. The programmer 5 of the present invention can interrogate the memory 15 of the cardiac rhythm management device 2 and download all of this information from the memory 15 of the device 2. A battery 19 supplies power to all components of the cardiac rhythm management device 2.

The programmer 5 of the present invention is constructed in a fashion somewhat analogous to a personal computer. In addition to the transmitter/receiver 102 used for communication with implantable cardiac rhythm management devices, the programmer 5 includes a processor 103, memory and storage 104, and a network interface card 105 so the programmer 5 can be attached to a network 7 as shown in FIG. 1. The programmer 5 also includes a user interface card. User interface card 106 provides ports for attaching a display, a keyboard and mouse, all of which make up the user interface of the preferred embodiment. The programmer 5 also includes a printer port 107 for attaching printer 6 to the programmer 5. Additionally, the programmer may have a built-in printer.

Ideally, the present invention incorporates at least two databases or, alternatively, a single database having two parts. For ease of explanation, the terms "first database" and "second database" will be used to refer to situations where either separate databases exist or where they are combined into a single database having two parts. As used herein, "database" refers to any mechanism used to store data in an organized fashion. The first database includes a plurality of report formats. Each report format has at least one variable data field. The second database contains data used to complete the variable data fields of the report formats of the first data base. Thus, the first and second databases work together to create various reports. The databases can reside on the programmer 5 and the data is then stored in memory/storage 104. Memory/storage 104 can be any type or combination of memory, hard drive or removable media. If the programmer 5 is attached to a network via network interface card 105 as shown in FIG. 1, the databases can reside on any computer (such as computers 8, 9, 10 or 11) attached to the network 7 so long as the network 7 is designed to permit the programmer 5 to send data to and retrieve data from the network.

Figure 3:
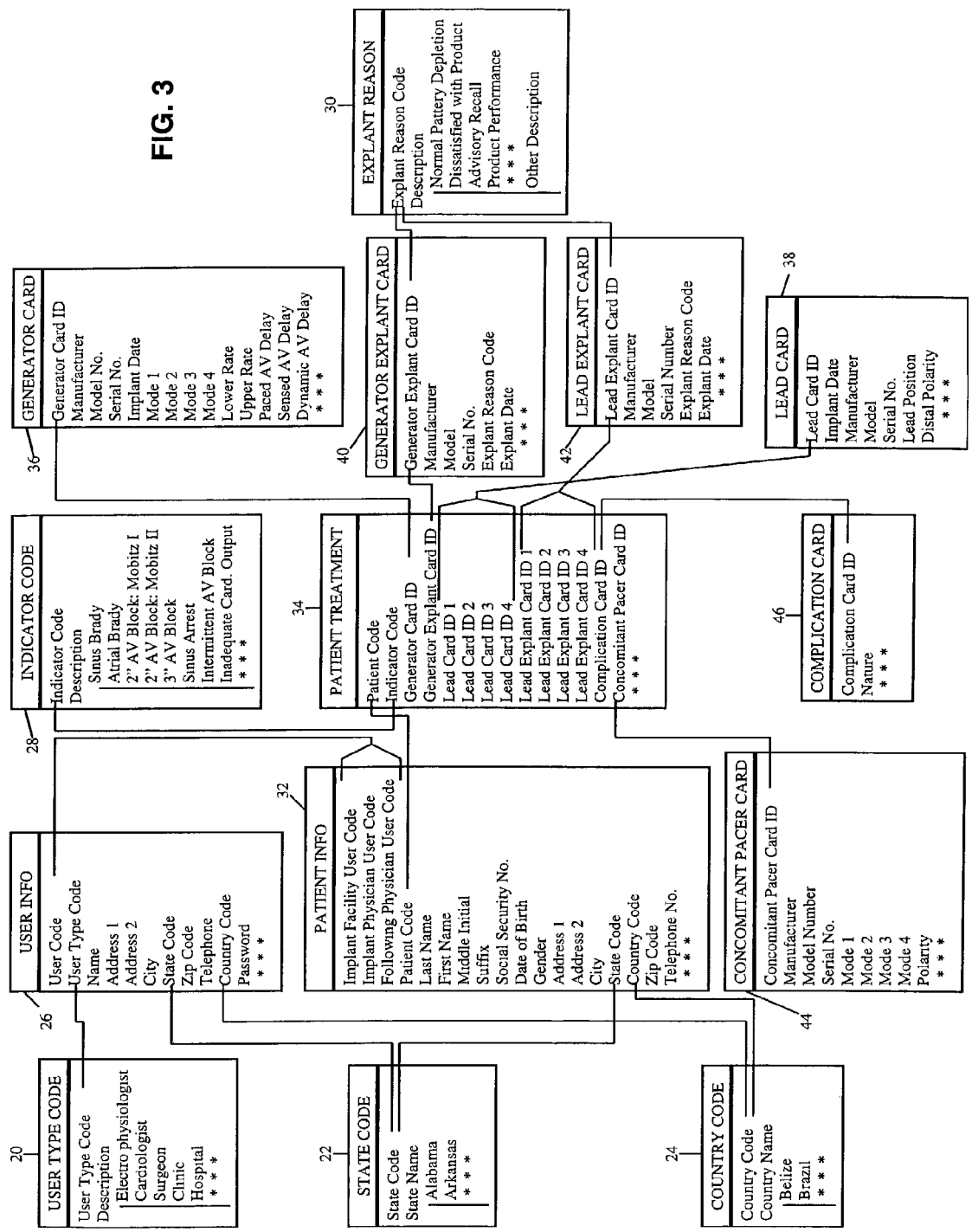
FIG. 3 is a data organization table.

The data structure of one embodiment of such a second database is shown in FIG. 3. As shown, the database is a relational database. Other types of databases and other data structures can be used without deviating from the invention. In FIG. 3, the data is stored in a plurality of tables linked together by various fields. Relational database management software, such as that manufactured by Microsoft or Oracle, permits database developers to design tables, establish relationships between the tables, use queries to study and organize the data in a meaningful way, and design reports that can be printed. In the present invention, printer 6 can be used to print reports, including warranty validation and lead registration reports.

FIG. 3 shows the data organized into 14 tables. Several of these tables are used as drop-down lists. For example, table 20 is used to identify different types of users or medical providers with a user code. Medical providers typically will include electrophysiologists, cardiologists, cardiovascular surgeons, clinics, hospitals, or the like. In table 20, each different provider type is associated with a code. Table 22 is used in this same fashion to associate state names with state codes. Likewise, table 24 is used to associate county names with codes.

Tables 20, 22 and 24 are all used when collecting specific information related to specific medical providers or users. Such specific information is maintained in the user information table 26. In table 26, medical providers are each assigned a unique user code. Associated with the user code is the user's name, address and telephone number. Table 20 is used to select the correct user type code to be associated with the user. Likewise, tables 22 and 24 are used to complete the state and county information for each specific user. Users can be assigned a password that may be required as a security measure to prevent unauthorized use of the programmer 5 or unauthorized access to the data in the database. When the user enters the user's user code and password at the beginning of a session, information related to the user can be automatically associated with each patient treated during the session.

Essentially all of the data contained in tables 20–26 can be entered once and used repeatedly as the programmer 5 is used to treat different patients 1. This saves substantial time and also ensures accuracy. Other tables can also be created before the programmer 5 is used to treat patients. For example, table 28 is used to associate indicator codes with different medical conditions that may warrant treatment of a patient 1 with a cardiac rhythm management device 2. In table 28 a separate indicator code is associated with each such condition. Similarly, there are times when a cardiac rhythm management device or a lead might be explanted and replaced with a new cardiac rhythm management device 2 and lead system 4. Table 30 is used to associate separate explant reason codes with descriptions of the reasons for such an explant. Again, tables 28 and 30 can be used as drop-down menus to speed patient data entry and ensure accuracy.

The essence of the data structure shown in FIG. 3 are the tables 32, 34, 36, 38, 40, 42, 44 and 46. These tables are used to store data related to individual patients and the specific treatment provided to the individual patients.

Table 32 is used to assign a patient code to each individual patient and associate census data with the patient code. Such census data includes the patient's name, Social Security number, gender, data of birth, address and telephone number. Table 32 also is used to associate up to three user codes with the patient code of each individual patient. These user codes include the user code of the implant facility, the user code of the implanting physician, and the user code of the physician who will be providing follow-up services for the patient. If desired, the data structure can be modified to permit more than three users to be associated with a patient.

Data related to the specific treatment provided for each individual patient is collected and maintained in table 34 and a plurality of "cards" 36–46. Table 34 is used to associate the patient code of each individual patient with an indicator code from table 28, a generator card 36, one or more lead cards 38 (there will be a separate lead card for every lead implanted in a multi-lead treatment situation), a generator explant card 40 if an earlier implanted cardiac rhythm management device was removed as part of the procedure, a lead explant card 42 for each lead explanted if one or more earlier implanted leads are explanted as part of the procedure, a concomitant pacer card 44 if the patient has both a pacer and another cardiac rhythm management device 2, and a complication card 46 if there were any complications during the procedure. Table 34 can be viewed as a "card index" for the cards 36–46. Cards 36–46 are simply additional tables in the database. These tables, like all the tables, can be combined into a fewer number of tables. Additional tables can also be added if desired.

While FIG. 3 shows a highly advantageous data structure, it should be noted that additional fields can be added to any of the tables 20–46 to collect additional data. Also, other tables can be added to the data structure. For example, a table including manufacturer codes and associated manufacturer names can be added and associated with tables 36–44 to serve as a drop-down menu when completing the manufacturer information on these tables. A table associating model numbers of devices made by each manufacturer could be created and used as a drop-down menu to be used when completing the model number fields on tables 36–44. Likewise, a table could be created to establish an association between a particular model of cardiac rhythm management device and a file containing a form of the first database intended to be used with that model. Multiple tables can also be combined into a single table if desired. For example, a data structure that combines tables 32 and 34 into a single table would clearly fall within the scope of this invention. With the foregoing in mind, use of the present invention will now be described.

When a patient is to be treated with a cardiac rhythm management device 2 and/or lead system 4, the implanting physician logs onto the programmer 5 by entering his or her user code and password. The system then assumes that the physician is the implanting physician. The programmer 5 has also been pre-programmed to use the correct implant facility user information based upon the facility where the programmer 5 is located. The user then enters certain patient information, i.e. the patient information in table 32. The system automatically assigns a patient code to each new patient.

As the cardiac rhythm management device 2 (and lead system 4) is implanted and programmed, additional information is collected using the programmer 5. If a pulse generator is explanted, the data for a generator explant card 40 is entered either using the programmer's keyboard, by telemetering the information between the explanted pulse generator and the programmer, or both. For example, the manufacturer, model number and serial number can be telemetrically retrieved from the explanted pulse generator by the programmer 5. This explant data is automatically inserted by the programmer's processor into the database. Other explant data can be supplied using the programmer's keyboard, or mouse or some other input device associated with the programmer 5. Likewise, if one or more leads are explanted, the user interface of the programmer 5 (i.e. the mouse, keyboard, etc.) can be used to record the manufacturer, model serial number and explant reason code for each lead explanted. A separate explant lead card 42 is generated for each explanted lead. The lead explant card ID codes for these cards 42 are automatically supplied to tables 34 and 42 by the programmer 5.

Information related to the new generator 2 implanted during the procedure can be collected in a similar fashion. As the generator 2 is programmed by the programmer 5 through the telemetry process, the information for the generator card 36 is automatically supplied to the database (and particularly generator card 36) by the programmer 5 to provide an accurate record of the manner in which the generator 2 was programmed. Information for each lead card 38 will typically need to be supplied using the user interface of the programmer 5.

If there is a concomitant pacer implanted in the patient, the programmer 5 can detect its presence and can download from the concomitant pacer much of the information necessary to complete the concomitant pacer card 44. Finally, the user provides any additional information needed for card 44 as well as a narrative regarding any complications which is stored on the complications card 26.

Figure 4:
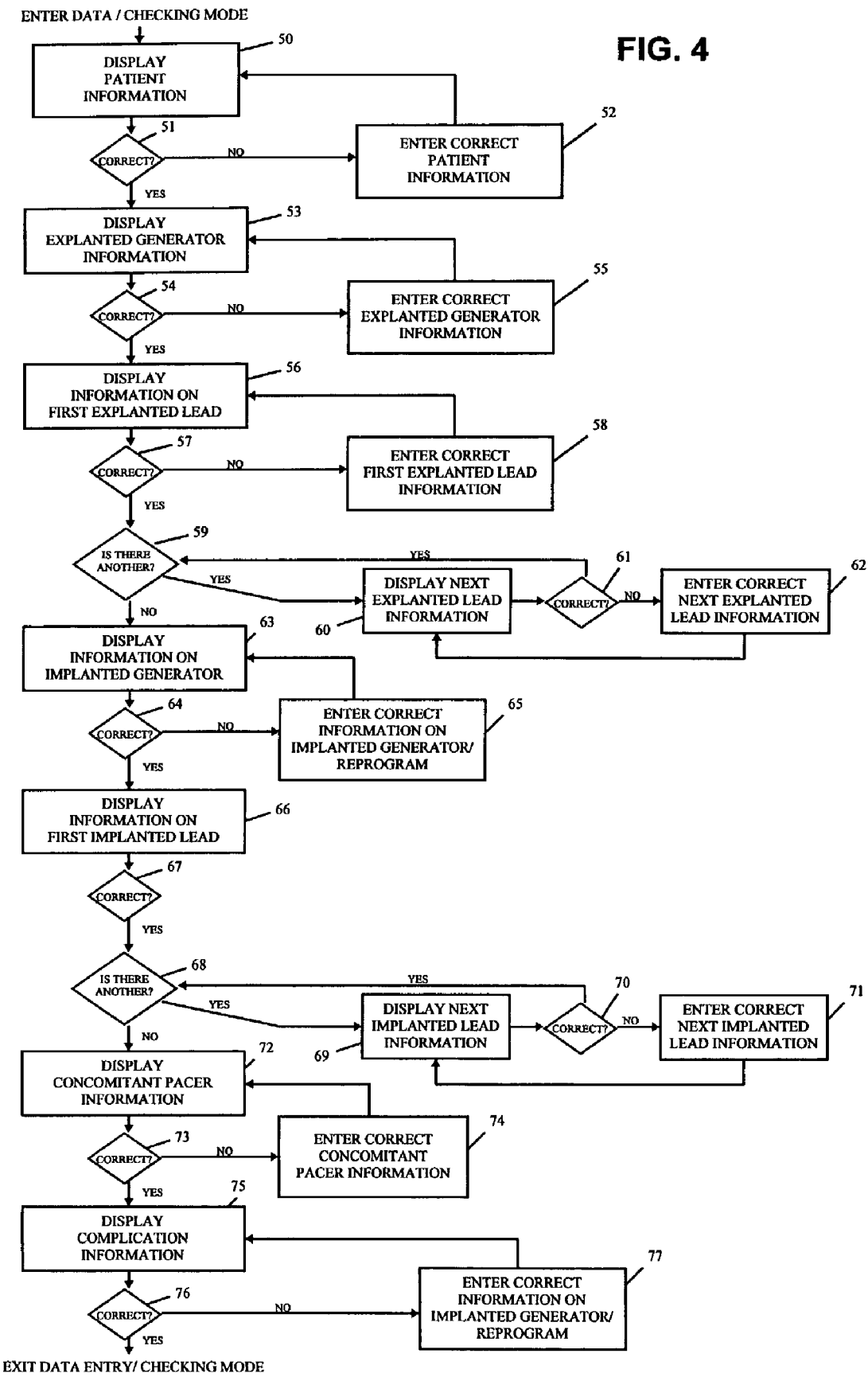
FIG. 4 is a flow chart having the data entry/checking mode of the present invention.

The programmer 5 of the present invention is programmed to include one or more subroutines for entering, checking and correcting information contained in the database. These will typically be performed to ensure the accuracy and completeness of the information collected. FIG. 4 is a flow chart showing such a subroutine.

As shown in FIG. 4, the programmer 5 enters a data entry/checking mode. At step 50, the programmer displays the patient information in the patient information table 34 related to the patient being treated. The data can, of course, be displayed in a user friendly manner so it is easy to read and quickly check.

Step 51 prompts the user to either enter a command signifying the information has been checked and is correct or enter a command indicating the data is incorrect. If the data is incorrect, the program goes to step 52 and the user is prompted to enter the correct patient information. The program cycles through steps 50, 51 and 52 until the user enters a command signifying all of the patient information is correct.

Once the patient information is correct, the programmer advances to step 53 and information related to the explanted generator, if any, is displayed. This data comes primarily from table 40. At step 54, the user is prompted to enter a command either signifying the information is correct or not correct. If the information is not correct, the program proceeds to step 55, attempts to interrogate the memory of the explanted cardiac rhythm management device, and prompts the user to enter any information which could not be downloaded through such an interrogation process. The program continues to cycle through steps 53, 54 and 55 until all of the information is correct and the user enters a command indicating the information is correct. When the programmer 5 receives such a command, the program advances to step 56 and information related to the first explanted lead is displayed.

As indicated above, one or more leads may be explanted during a procedure. Each explanted lead has its own explanted lead card 42. The program cycles through steps 56–62 until the data on each lead explant card 42 is verified. The user is provided with various prompts throughout this process. Specifically, at step 56, information from the first lead card 42 is displayed. At step 57, the user is prompted to indicate whether the information is correct. If not, the program cycles through to step 58 and back through steps 56 and 57 until the user is satisfied that all the information is complete and accurate. At step 59, the system checks to see if there is another explanted lead card. Alternatively, the user can indicate if there is another explanted lead. The software cycles through steps 59, 60, 61 and 62 until information on all explanted leads has been correctly entered on separate explanted lead cards 42 for each explanted lead.

Now that information related to the patient and explanted equipment has been entered into the appropriate tables of the database and checked, the system gathers and checks information related to implanted equipment starting with the implanted generator (i.e. the cardiac rhythm management device 2). At step 63, the programmer 5 collects, stores and displays the data in table 36. This step provides the advantage of ensuring that the generator 2 has been programmed as intended by the user. The user is prompted at step 64 to verify all of the information stored in table 36. If any information is incorrect, the software proceeds to step 65 where the user enters the correct information which can first be used by the programmer 5 to reprogram the generator 2, read back by the generator 2 to the programmer 5, stored in table 36 and displayed on the programmer's display. When the user is satisfied that the generator 2 is properly programmed and the data in table 36 is, therefore, correct, the user indicates that the information is correct and the software proceeds to step 66.

Steps 66–71 are used to verify information related to each implanted lead. For each such lead, a lead card 38 is created. This portion of the program works in a nearly identical way to steps 56–62 described above. The only significant difference, other than the specific information contained in cards 38 versus cards 42, is that steps 56–62 relate to explanted leads and steps 66–71 related to implanted leads.

Once all of the lead data is correct, the software advances to step 72. Steps 72, 73 and 74 are used to collect, store and check data related to a concomitant pacer, if one is present. Step 74 is completed by the programmer 5 interrogating the memory of the concomitant pacer, by prompting the user to input required data, or both.

During any surgical procedure, complications may arise. Steps 75–77 are used to collect, record in table 46 and check information related to any complications that occurred. After this is complete, the software exits the data entry/checking mode.

In addition to relying upon error checking by the user, certain automated error checking routines may be added to the programmer's software. This software may be designed to check the database to ensure that a set of required fields are all completed. The set of required fields may change based upon the type of cardiac rhythm management device and/or lead system used. Also, the programmer's software can be designed to automatically check data taking into the universe of possible acceptable combinations of data. For example, the program can be programmed to know what lead systems are compatible with what cardiac rhythm management devices. If the user selects an incompatible combination, the system can be programmed to advise the physician. Such error checking schemes can be applied to virtually any of the data collected by the programmer.

Figure 6:
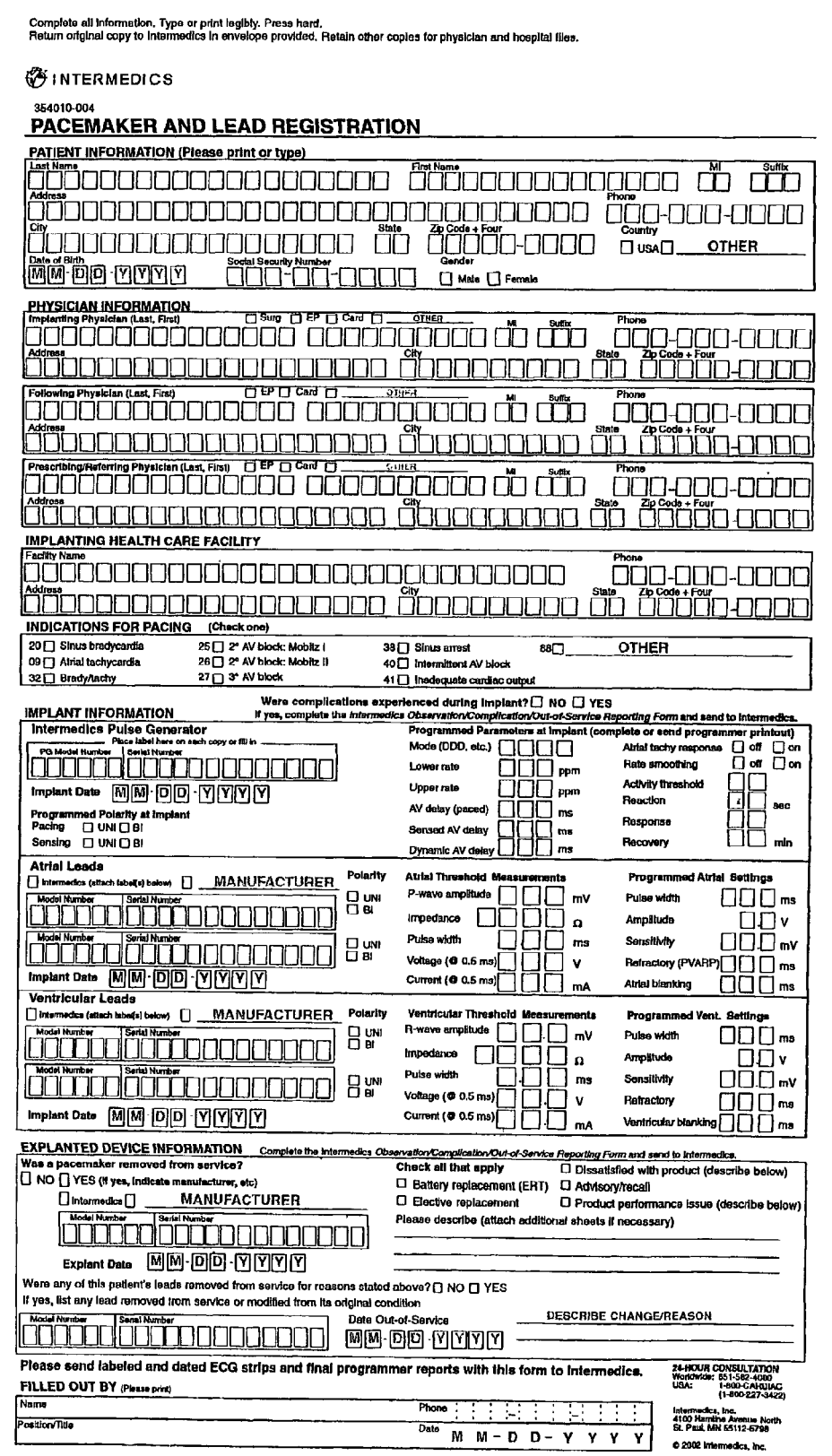

The system of the present invention uses the data in the database to generate, transmit to other computers on the network, and/or print a variety of reports. The system can also transmit the reports to facsimile machines such as facsimile machine 13. Such reports can include a warranty and lead registration report. Examples of the forms of two such reports are shown in FIGS. 5 and 6. When these forms are printed or transmitted electronically, preferably all of the data required by the form is automatically filled in from the database. Of course, people using the system of the present invention will need to take the steps necessary to comply with HIPAA legislation and other data privacy laws. Templates for such forms can be created in advance and the system will know which form to use based upon data in the database.

FIG. 5 is a sample warranty and registration form for use when the device 2 is a pacemaker. When the system of the present invention is used and the implanted device is a pacemaker manufactured by Guidant Corporation, the programmer will automatically select this form and fill in all of the required information using the data in the database. Specifically, the device identification information required by the form is supplied by table 36, the patient information by table 32, the physician and implanting healthcare facilities information by tables 32 and 26, the indications information by tables 34 and 28, the implant and lead information from tables 36 and 38, the explant information from tables 40 and 42, and complications information from table 46.

FIG. 6 is a sample of a form used for a heart failure device. Again, the programmer selects the correct form based upon the manufacturer and model number of the device implanted in the patient. The programmer is also able to automatically supply all of the information required to complete the form.

Once the proper form has been selected and completed, the system of the present invention can be used to print hard copies of the form and/or to transmit the data to one or more computers for further processing and storage. The data could be sent to the computers of the implanting physician, the following physician, the patient's primary care physician, the healthcare facility, the device manufacturer, etc. Generally, the manually completed forms of the prior art were used to manually enter data into some or all of these computer systems. Electronic transmission of this data as contemplated by the present invention, reduces costs and creates efficiency by eliminating the need to manually record and then manually re-enter this data into each of these computers.

Those skilled in the art will recognize that the data may change over time. For example, the patient may move or get a new telephone number. Therefore, the system of the present invention is designed so data in the database can be edited and the revised information can be transmitted in all the same ways discussed above.

Of course, the system of the present invention can be implemented in a less sophisticated fashion than that represented by the preferred embodiment described above. For example, the system could simply include a table linking various warranty and registration forms to various model numbers for cardiac rhythm management devices. When the model of a device is retrieved from memory, the correct form or set of forms for the device is displayed and the user is prompted to supply the data required by the form. Even in less sophisticated implementations, some data for the forms can be retrieved from the cardiac rhythm management device or retrieved from tables of data previously stored in the programmer's memory/storage.

The foregoing description has been provided to comply with the disclosure requirements of the patent statutes. It is not intended to describe every conceivable way of practicing the invention. The full scope of the invention is not intended to be limited by this disclosure. Instead, the scope of the invention is defined by the following claims which are to be given their broadest reasonable interpretation and the benefit of the full range of equivalents.

What is claimed is:

1. A system for creating records related to the use of medical products with particular patients comprising:
   a. a plurality of medical products each having machine readable data, said data comprising at least indicia of the type of medical product and indicia of the specific identity of the medical product;
   b. at least one apparatus including data, storage, a user interface, an output device and a data reader all in communication with a processor that controls said apparatus based upon a programmed set of instructions;
   wherein said storage contains at least user information, patient information, device information, and treatment information, and a plurality of different treatment record formats, said different treatment record formats being associated with different types of medical product, at least some of said information supplied to the storage using said user interface and at least some of said information supplied to said storage using said data reader to read machine readable data from said medical products,
   wherein said processor creates a treatment record for a specific medical product by selecting a treatment record format corresponding to the type of said specific medical product and populated fields of the selected treatment record format using said information associated with the specific medical product, and
   wherein said processor outputs the created treatment record.

2. The system of claim 1 wherein said apparatus is a network having multiple nodes.

3. The system of claim 2 where a first portion of said storage is located on a first node of network and a second portion of said storage is on a second node of said network.

4. The system of claim 1 wherein said processor outputs said treatment record to at least one device, said device comprising either a display, printer, facsimile machine or computer.

5. A method by which a user of a programmer can generate a registration card of a correct format for a programmable cardiac rhythm management device implanted in a patient, said cardiac rhythm management device having a memory for storing its type, its identity, and parameters with which it has been programmed, said method comprising:
   (a) using said programmer to interrogate the memory of a cardiac rhythm management device to determine its type, its identity, and parameters with which it has been programmed;
   (b) storing data derived from interrogating the memory of the cardiac rhythm management device in a database, said database also including patient data and user data;
   (c) selecting from a set of report formats a correct format for the registration card for said cardiac rhythm management device based upon its type;
   (d) inserting into the selected format data stored within said database required to complete the registration card;
   (e) prompting the user of the programmer to supply data required to complete the registration card but not contained within said database;
   (f) transmitting the registration card.

6. The method of claim 5 wherein the patient data within said database includes information which can be used to identify and contact a patient in whom said programmable cardiac rhythm management device has been implanted.

7. The method of claim 5 wherein said user data within said database includes information which can be used to identify and contact the user.

8. The method of claim 5 wherein said database includes data related to at least one lead used in conjunction with the cardiac rhythm management device.

9. The method of claim 5 wherein said database includes information related to the patient's medical condition.

10. The method of claim 5 wherein said database includes information related to medical devices explanted from the patient.

11. The method of claim 5 wherein said transmitted registration card is re-transmitted to a printer which prints the registration card.

12. The method of claim 5 wherein said programmer includes a network interface card.

13. The method of claim 12 wherein said network interface card is used to connect the programmer to a network of devices and the programmer transmits said registration card to at least one other device on the network.

14. A system for generating warranty and registration records related to medical products used to treat patients, at least some of said medical products having a memory in which an indicia of the type of medical product and an indicia of the specific identity of the medical product is stored, said system including:
   a. a first database containing a plurality of warranty and registration record formats and at least some of said formats having a plurality of data fields;
   b. a second database for storing data related to patients, medical products used to treat the patients, at least one physician who treats the patients, and at least one facility where the patients are treated; and
   c. a device that interrogates the memory of a medical product to retrieve from said memory of said medical product said indicia of the type of medical product and said indicia of the specific identity of the medical product, selects a warranty and registration record format from the plurality of record formats stored in the first database based upon at least some of said indicia retrieved from said memory of said medical product, completes fields in the selected warranty and registration record by selecting and using data from the second database to create a warranty and registration record, and transmits said record.

15. The system of claim 14 further including a printer to which said record is transmitted for printing.

16. The system of claim 14 further including a facsimile machine to which said record is transmitted.

17. The system of claim 14 wherein said device is a first node on a network containing a plurality of nodes.

18. The system of claim 17 wherein said first database is stored on a node of the network other than said first node.

19. The system of claim 17 wherein said second database is stored on a node of the network other than said first node.

20. The system of claim 17 wherein said record is transmitted from said first node to at least one other node on said network.

21. The system of claim 14 wherein said first database contains selectable report formats, in addition to said warranty and registration record formats.

22. The system of claim 21 wherein said device can create a report by selecting one of said selectable report formats from said first database and populates at least one data field of said selected report format using data stored in said second database.

23. A system for creating warranty and registration records related to medical products used with particular patients comprising:
    a. a plurality of medical products each having machine readable data, said data comprising at least indicia of the type of medical product and indicia of the specific identity of the medical product;
    b. at least one apparatus including data, storage, a user interface, an output device and a data reader all in communication with a processor that controls said apparatus based upon a programmed set of instructions;
    wherein said storage contains at least user information, patient information, device information, and treatment information, and a plurality of warranty and registration record formats, each of said warranty and registration record formats being associated with a type of medical product and having a plurality of data fields, at least some of said information supplied to the storage using said user interface and at least some of said information supplied to said storage using said data reader to read machine readable data from said medical products,
    wherein said processor creates a warranty and registration record for a specific medical product by selecting the warranty and registration record format corresponding to the type of said specific medical product and populating fields of the selected warranty and registration report format using said information associated with the specific medical product, and
    wherein said processor outputs said warranty and registration record.

24. The system of claim 23 wherein said storage contains selectable report formats, in addition to said warranty and registration record formats.

25. The system of claim 24 wherein said apparatus can create a report by selecting one of said selectable report formats and populates at least one of said plurality of data fields of said selected report formation using said information in said storage.

26. The system of claim 23 wherein said apparatus is a network having multiple nodes.

27. The system of claim 26 wherein a first portion of said storage is located in a first node of said network and second portion of said storage is located on a second node of said network.

28. The system of claim 23 wherein said processor outputs said warranty and registration record to at least one device, said device comprising either a display, a printer, a facsimile machine or a computer.

29. The system of claim 23 wherein said indicia of the type of medical product and the indicia of the specific identity of the medical product are both contained within a serial number of the product.

30. The system of claim 23 wherein said indicia of the type of medical product is a model number and said indicia of the specific identity of the medical product is a serial number.

31. The system of claim 23 further including a printer for printing said output warranty and registration record generated by said processor.

32. The system of claim 23 wherein said user interface allows a user to add data to or edit certain data contained in the storage.

33. The system of claim 32 wherein said user interface prompts the user to supply additional data when information not already in the storage is required to complete a field of the selected warranty and registration record.

34. The system of claim 23 wherein said medical products are implantable medical products.

35. The system of claim 34 wherein said implantable medical products are cardiac rhythm management devices.

36. The system of claim 34 wherein said apparatus is an external programmer for said implantable medical products.

37. The system of claim 36 wherein said external programmer is a node on a network containing a plurality of nodes and said external programmer can transfer the warranty and registration records it generates to at least one other node on said network.

38. The system of claim 23 wherein said apparatus is part of a network of devices and is capable of transferring the warranty and registration records it generates to other network devices.

39. The system of claim 23 wherein at least one of said medical products is programmable.

40. The system of claim 23 wherein said apparatus outputs warranty and registration records it generates to a facsimile machine.

41. The system of claim 23 wherein said user information contains data related to at least one facility where patients are treated.

42. The system of claim 23 wherein said storage contains data related to at least one physician who treats said patients.

* * * * *